United States Patent [19]

Dorn

[11] Patent Number: 4,919,935
[45] Date of Patent: Apr. 24, 1990

[54] INSECTICIDAL COMPOSITIONS
[75] Inventor: Silvia Dorn, Dielsdorf, Switzerland
[73] Assignee: R. Maag AG, Dielsdorf, Switzerland
[21] Appl. No.: 245,691
[22] Filed: Sep. 15, 1988
[30] Foreign Application Priority Data
Sep. 30, 1987 [CH] Switzerland ............... 3810/87
[51] Int. Cl.$^5$ .................................. R01N 25/00
[52] U.S. Cl. ........................ 424/405; 514/63; 514/461
[58] Field of Search ............ 424/405; 514/469, 63
[56] References Cited
U.S. PATENT DOCUMENTS

| | | | |
|---|---|---|---|
| 3,111,539 | 11/1963 | Bocker et al. | 260/479 |
| 3,310,467 | 3/1967 | Kramer et al. | 167/42 |
| 3,736,338 | 5/1973 | Gates et al. | 260/340.5 |
| 3,781,301 | 12/1973 | Nikles et al. | 260/327 U |
| 4,215,139 | 7/1980 | Fischer et al. | 424/300 |
| 4,524,150 | 6/1985 | Adalsteinsson | 514/469 |
| 4,595,679 | 6/1986 | Broadbent | 514/938 |
| 4,775,664 | 10/1988 | Schubert et al. | 514/63 |

OTHER PUBLICATIONS

Pesticide Manual, 5th Edition (1977), British Crop Protection Council, pp. 30, 445 and 213.
Osbrink et al., Journal of Economic Entomology, vol. 79, No. 1, pp. 135–140 (1986).
Abstract of Becker et al., Meded. Fac. Landbouwwet Rijksuniv. Gent., 52, No. 2b 455–62 (1987).

Primary Examiner—Thurman K. Page
Assistant Examiner—P. L. Prater
Attorney, Agent, or Firm—Wenderoth, Lind & Ponack

[57] ABSTRACT

The invention is concerned with insecticial compositions which contain as active substances (a) ethyl [2-(4-phenoxyphenoxy)ethyl]carbamate and (b) 2,3-isopropylidenedioxyphenyl methylcarbamate or 2-isopropoxyphenyl methylcarbamate or 2-(1,3-dioxolan-2-yl)phenyl methylcarbamate and, optionally, inert carrier material, and with the manufacture and the use of such compositions.

7 Claims, No Drawings

INSECTICIDAL COMPOSITIONS

BRIEF SUMMARY OF THE INVENTION

The invention relates to insecticidal compositions which contain as active substances (a) ethyl [2-(4-phenoxyphenoxy)ethyl]carbamate and (b) 2,3-isopropylidenedioxyphenyl methylcarbamate or 2-isopropoxyphenyl methylcarbamate or 2-(1,3-dioxolan-2-yl)phenyl methylcarbamate and to the manufacture and use of such compositions.

DETAILED DESCRIPTION OF THE INVENTION

The invention relates to insecticidal compositions. These contain as active substances
(a) ethyl [2-(4-phenoxyphenoxy)ethyl]carbamate and
(b) 2,3-isopropylidenedioxyphenyl methylcarbamate or 2-isopropoxyphenyl methylcarbamate or 2-(1,3-dioxolan-2-yl)phenyl methylcarbamate.

Component (a) is known under the name fenoxycarb and components (b) are known under the names bendiocarb, propoxur and dioxacarb, respectively. The preferred component (b) is 2,3-isopropylidenedioxyphenyl methylcarbamate (bendiocarb).

The compositions in accordance with the invention accelerate the onset of the insecticidal activity and enhance the efficacy against mixed populations of a great variety of insect types. Moreover, synergism occurs in many cases. Finally, the development of resistance can be broken with the compositions in accordance with the invention.

The composition in accordance with the invention is effective against a great variety of harmful insects in houses, sheds, in water and in the open air, on plants and animals, on stores and materials, such as e.g. against flies and mosquitos (Musca spp., Aedes spp., Culex spp., Anopheles spp., *Lucilia sericata*, etc.); cockroaches (*Blattella germanica, Blattella orientalis, Periplaneta americana*, etc.); pests of materials and stores (*Tineola bisselliella, Anthrenus scropholariae*, Attagenus spp., Tribolium spp., Sitophilus spp., *Rhizopertha dominica*, Oryzaephilus spp., Ephestia spp., Plodia spp., *Sitotroga cerealella*, etc.); ants (Atta spp., Acromyrmex spp., Pogonomyermex spp., Iridomyrmex spp., Pheidole spp., Mormonium spp., Camponotus spp., Lasius spp., Phormica spp., Myrmica spp., Solenopsis spp., Tetramorium spp., etc.); fleas (*Xenopsylla cheopsis, Ctenocephalides felix*, etc.); termites (Reticulotermes spp., Macrotermes spp., etc.).

The components (a) and (b) can be compounded according to any method which is usual for such compounds and the process for the manufacture of the compositions in accordance with the invention comprises mixing component (a) with a component (b) and, where required, with an inert carrier material.

The weight ratio of component (a) to component (b) conveniently lies in the range of about 1:0.01 to 1:10, preferably of about 1:0.01 to 1:1.

When desired, the components (a) and (b) can be dissolved in a water-immiscible solvent such as, for example, a high boiling hydrocarbon, which conveniently contains dissolved emulsifying agent, so that the solution becomes self-emulsifying upon addition to water.

The components can also be mixed with a wetting agent in the presence or absence of an inert diluent to form a wettable powder which is soluble or dispersible in water or they can be mixed with inert diluents to form a solid or pulverous product.

As inert diluents, including pulverous or finely divided solids, with which the components (a) and (b) can be processed there come into consideration kaolin, clays, sands, talc, mica, fertilizers and the like, whereby such products can be present either in the form of dusts or as materials having a larger particle size.

The wetting agents can be anionic compounds such as, for example, soaps; fatty sulphate esters, e.g. dodecyl sodium sulphate, octadecyl sodium sulphate and cetyl sodium sulphate; fatty-aromatic sulphonates, e.g. alkylbenzenesulphonates and butylnaphthalenesulphonates; and more complex fatty sulphonates. e.g. the amide condensation products of oleic acid and N-methyltaurine and the sodium sulphonate of dioctyl succinate.

The wetting agents can also be non-ionic wetting agents such as, for example, condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; or the products which are known as block copolymers of ethylene oxide and propylene oxide.

Finally, the wetting agents can be cationic agents such as, for example, cetyltrimethyl- ammonium bromide and the like.

The insecticidal composition in accordance with the invention can also be present in the form of an aerosol, in which case a co-solvent and a wetting agent are conveniently used in addition to the propellant, which is suitably a polyhalogenated alkane such as dichlorodifluoromethane.

The following types of formulation stand in the foreground: powders, dusts, granulates, solutions, suspensions, emulsions, emulsifiable concentrates, pastes, fumigants, atomizing compositions, baits and aerosols.

The compositions in accordance with the invention can be used as formulated mixtures of the two components (a) and (b) or can be prepared immediately prior to use from the two separately formulated components, e.g. the two components (a) and (b) formulated as wettable powders are introduced into water, whereby a spray liquor results.

The concentration of active substances, i.e. component (a) and component (b), in the insecticidal compositions in accordance with invention can vary within a wide range, for example between about 0.002 wt. % and about 95 wt. %, preferably between about 0.5 and about 90 wt. %. The composition can be present, for example, in a form which is suitable for storage and transport. In such formulations, e.g. spray powders, the total active substance concentration is normally in the higher range, preferably between 0.25 and 95 weight percent, especially between 0.25 and 80 wt. %. These formulations can then be diluted e.g. with inert materials, especially with water, to give active substance concentrations which are suitable for practical use, i.e. preferably about 0.002 to 2 wt. %, especially about 0.05–0.6 wt. %. The active substance concentrations can, however, also be lower or higher.

In their various fields of use the insecticidal compositions in accordance with the invention can be used in different ratios.

The active substance combinations in accordance with the invention are conveniently used in an amount of 1–10,000 mg/m² of ground and treatment, preferably 10–100 g/ha of ground and treatment in the case of large-surface external treatments, or 10–100 mg/m² of active substance (a) and 100–10,000 mg/m² of active substance (b) are conveniently used for special treatments (e.g. indoor uses).

EXAMPLE 1

(adulticide)

*Musca domestica*

Test insect: *Musca domestica* (common housefly), multi-resistant strain.

Test method: Treated filter strips are placed in a plastic beaker. 10 female flies are place in each beaker. The water supply of the flies is provided by means of a moist wad of cotton wool in the bottom of the plastic beaker. The incubation is carried out at 23° C. and 50% relative humidity. Test duration: 48 hours. The activity is expressed as the percentage reduction in the number of fully grown flies compared with the controls.

| Active substance [Component a and/or b] | Commercial formulation | Dosage $10^{-x}$ g active substance/cm² x = | Activity (%) |
|---|---|---|---|
| b | WP 80% | 4 | 17 |
| a | WP 25% | 4 | 0 |
| b in combination with a | WP 80% WP 25% | 4 4 | 65 |

Untreated controls: mortality 0%
b: 2.3-Isopropylidenedioxyphenyl methylcarbamate
WP: Wettable powder

EXAMPLE 2 (wettable powder)

| Fenoxycarb (100%) | 250 g |
|---|---|
| Bendiocarb (100%) | 250 g |
| Silicic acid, hydrated (solid diluent) | 150 g |
| Sodium lauryl sulphate (wetting agent) | 20 g |
| Sodium lignosulphonate (dispersing agent) | 50 g |
| Kaolin (solid diluent) | ad 1000 g |

Preparation:

The molten fenoxycarb is sprayed in a fine jet on to the silicic acid in a mixer so that a finely powdered mixture results. With continued intensive mixing there are subsequently added in sequence bendiocarb, sodium lauryl sulphate, sodium lignosulphonate and kaolin. This mixture is milled in an air-jet mill. For application, the thus-prepared spray powder can be stirred into water in the desired concentration and then gives a finely disperse spray liquor.

I claim:

1. An insecticidal composition wherein the insecticidally active substances consist essentially of:
   (a) ethyl[2-(4-phenoxyphenoxy)ethyl]carbamate and
   (b) 2,3-isopropylidenedioxyphenyl methylcarbamate or 2-isopropoxyphenyl methylcarbamate or 2-(1,3-dioxolane-2-yl)phenyl methylcarbamate and, optionally, inert carrier material, and the weight ratio of component (a) to component (b) lies in the range of about 10:0.01 to 1:10.

2. An insecticidal composition according to claim 1, wherein the component (b) is 2,3-isopropylidenedioxyphenyl methylcarbamate.

3. An insecticidal composition according to claim 1, wherein the weight ratio lies in the range of about 1:01 to 1:1.

4. A process for the manufacture of an insecticidal composition in accordance with claim 1, which process comprises mixing component (a) with component (b) and, optionally, with inert carrier material.

5. A process according to claim 4, wherein the component (b) is 2,3-isopropylidenedioxyphenyl methylcarbamate.

6. A process according to claim 4, wherein components (a) and (b) are mixed in a weight ratio of component (a) to component (b) in the range of about 1:0.01 to 1:10

7. A method for the control of harmful insects, which method comprises treating the locus to be protected or the insects themselves with an effective amount of an insecticidal composition in accordance with claim 1.

* * * * *